United States Patent
Para

(10) Patent No.: US 10,751,172 B2
(45) Date of Patent: *Aug. 25, 2020

(54) PUCKERING SEAL FOR REDUCED PARAVALVULAR LEAKAGE

(71) Applicant: St. Jude Medical, Cardiology Division, Inc., St. Paul, MN (US)

(72) Inventor: Andrea N. Para, St. Louis, MO (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 245 days.

This patent is subject to a terminal disclaimer.

(21) Appl. No.: 15/497,460

(22) Filed: Apr. 26, 2017

(65) Prior Publication Data

US 2017/0224482 A1 Aug. 10, 2017

Related U.S. Application Data

(63) Continuation of application No. 14/303,102, filed on Jun. 12, 2014, now Pat. No. 9,668,856.

(60) Provisional application No. 61/839,760, filed on Jun. 26, 2013.

(51) Int. Cl.
*A61F 2/24* (2006.01)

(52) U.S. Cl.
CPC .... *A61F 2/2418* (2013.01); *A61F 2220/0075* (2013.01); *A61F 2250/006* (2013.01); *A61F 2250/0069* (2013.01); *Y10T 29/49412* (2015.01)

(58) Field of Classification Search
None
See application file for complete search history.

(56) References Cited

U.S. PATENT DOCUMENTS

| | | |
|---|---|---|
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |

(Continued)

FOREIGN PATENT DOCUMENTS

| | | |
|---|---|---|
| DE | 19857887 A1 | 7/2000 |
| DE | 202008009610 U1 | 12/2008 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Leslie Lopez
(74) *Attorney, Agent, or Firm* — Lerner, David, Littenberg, Krumholz & Mentlik, LLP

(57) ABSTRACT

A heart valve assembly includes a heart valve, a self-expandable and collapsible stent, and a sealing member. The stent includes an inflow end and an outflow end and is configured to support the heart valve internally. The sealing member is connected to and extends circumferentially around the stent. The sealing member includes a plurality of radially outward extending protrusions comprising a fold of material of the sealing member.

18 Claims, 12 Drawing Sheets

(56) References Cited

U.S. PATENT DOCUMENTS

| | | |
|---|---|---|
| 5,855,601 A | 1/1999 | Bessler et al. |
| 5,935,163 A | 8/1999 | Gabbay |
| 5,961,549 A | 10/1999 | Nguyen et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,869,444 B2 | 3/2005 | Gabbay |
| 6,893,460 B2 | 5/2005 | Spenser et al. |
| 6,908,481 B2 | 6/2005 | Cribier |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,524,331 B2 | 4/2009 | Birdsall |
| RE40,816 E | 6/2009 | Taylor et al. |
| 7,585,321 B2 | 9/2009 | Cribier |
| 7,731,742 B2 | 6/2010 | Schlick et al. |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 9,034,032 B2 | 5/2015 | McLean et al. |
| 2002/0036220 A1 | 3/2002 | Gabbay |
| 2003/0023303 A1 | 1/2003 | Palmaz et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2005/0096726 A1 | 5/2005 | Sequin et al. |
| 2005/0256566 A1 | 11/2005 | Gabbay |
| 2006/0008497 A1 | 1/2006 | Gabbay |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |
| 2013/0197622 A1 | 8/2013 | Mitre et al. |
| 2014/0243966 A1 | 8/2014 | Garde et al. |
| 2014/0277422 A1* | 9/2014 | Ratz ............. A61F 2/2418 623/2.37 |

FOREIGN PATENT DOCUMENTS

| | | |
|---|---|---|
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.

(56) References Cited

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
U.S. Appl. No. 29/375,243, filed Sep. 20, 2010.

* cited by examiner

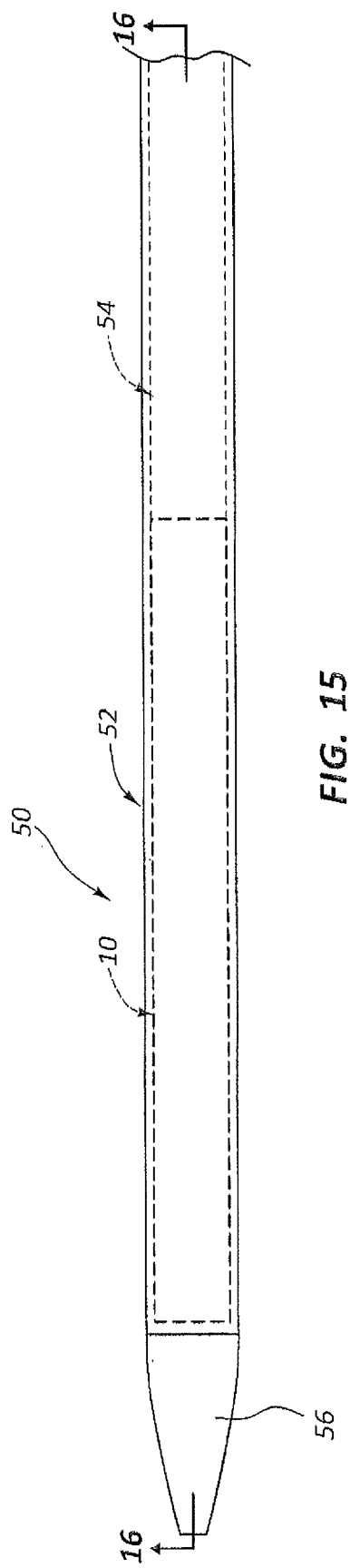
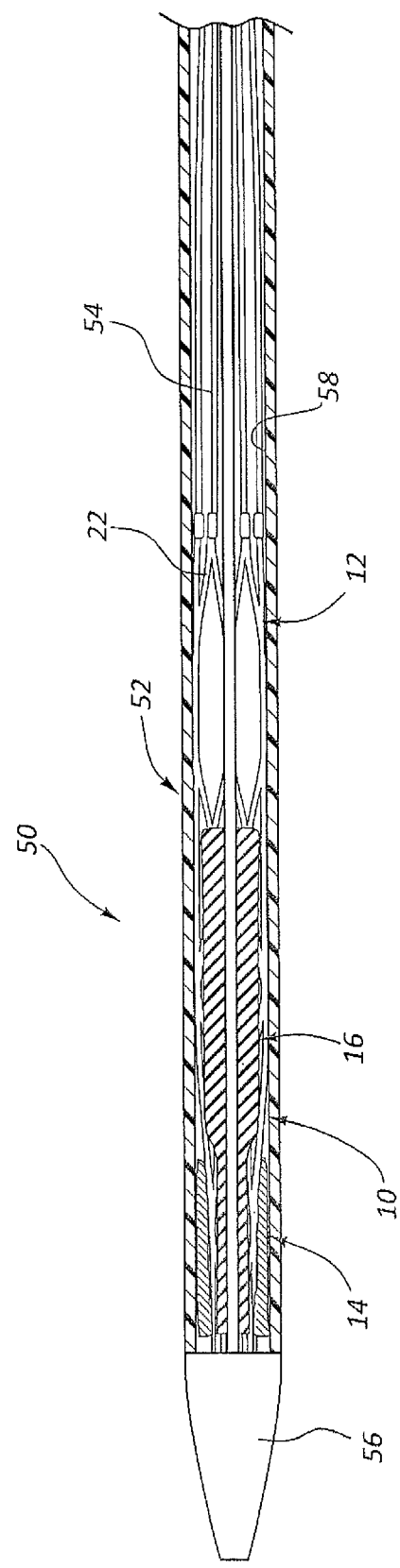
FIG. 15
FIG. 16

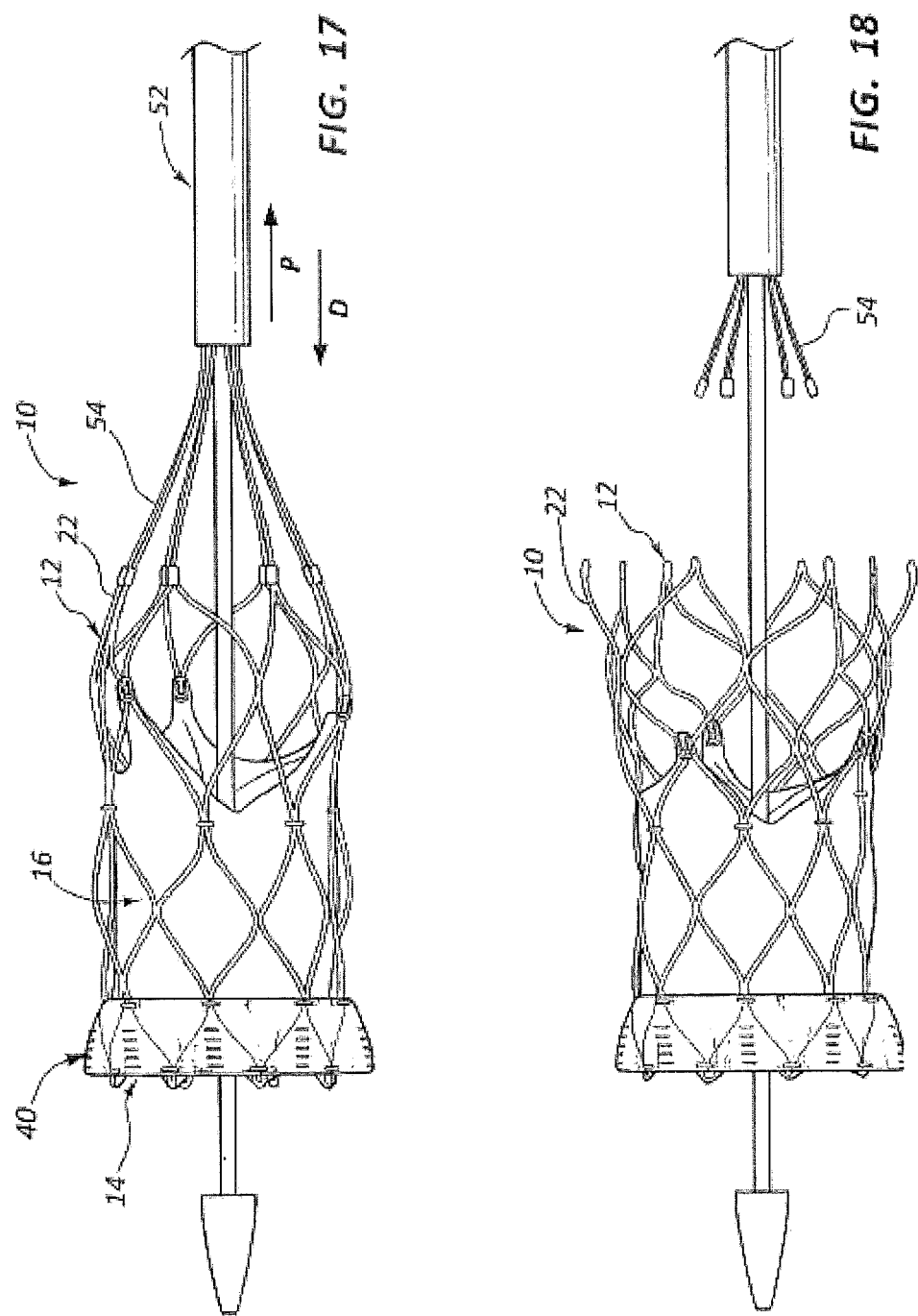

PUCKERING SEAL FOR REDUCED PARAVALVULAR LEAKAGE

CROSS-REFERENCES TO RELATED APPLICATIONS

This application is a continuation of U.S. patent application Ser. No. 14/303,102, filed Jun. 12, 2014, which claims the benefit of the filing date of U.S. Provisional Patent Application No. 61/839,760, filed Jun. 26, 2013, the disclosures of which are hereby incorporated herein by reference.

TECHNICAL FIELD

The present disclosure relates to replacement heart valves, and more particularly relates to collapsible heart valves and associated sealing devices and methods.

BACKGROUND OF THE INVENTION

Prosthetic heart valves may be formed from biological materials such as harvested bovine valves or pericardial tissue. These valves are typically fitted within a stent, which may be inserted into the heart at the annulus of the compromised native valve to replace the native valve. To perform an insertion procedure using a minimally invasive transcatheter technique, it may be necessary to compress the stent to a reduced diameter for loading into a delivery device.

Paravalvular (or perivalvular) leak (PVL) is a relatively rare complication related to the replacement of native heart valves. PVL describes a condition of blood flowing between the implanted valve structure and the cardiac tissue rather than through the implanted valve structure as desired. While most PVLs are hemodynamically non-significant, significant leaks may be problematic and require further intervention.

SUMMARY OF THE INVENTION

One aspect of the present disclosure relates to a heart valve assembly that includes a heart valve, a self-expandable and collapsible stent, and a sealing member. The stent includes an inflow end and an outflow end and is configured to support the heart valve internally. The sealing member is connected to and extends circumferentially around the stent. The sealing member includes a plurality of radially outward extending protrusions comprising a fold of material of the sealing member.

Another aspect of the present disclosure relates to a sealing member for use with a valve assembly. The sealing member includes a base configured for attachment to a self-expandable and collapsible stent. A plurality of protrusions are formed in a radially outward facing surface of the base and configured to provide a sealed interface between the valve assembly and an annulus at an implantation site.

Another aspect of the present disclosure relates to a method of manufacturing a valve assembly. The method includes providing a stent, a valve, and a sealing member. The stent has a self-expandable and collapsible construction. The sealing member includes a plurality of protrusions. The method further includes mounting the valve within the stent, and mounting the sealing member to the stent with the plurality of protrusions extending radially outward.

The foregoing and other features, utilities, and advantages of the invention will be apparent from the following detailed description of the invention with reference to the accompanying drawings.

BRIEF DESCRIPTION OF THE DRAWINGS

FIG. 15 is a side view of the heart valve assembly of FIG. 1 with a delivery system prior to deployment.

FIG. 16 is a cross-sectional view of the heart valve assembly and delivery apparatus of FIG. 15 taken along cross-section indicators 16-16.

FIG. 17 shows the heart valve assembly of FIGS. 15 and 16 partially deployed.

FIG. 18 shows the heart valve assembly of FIGS. 15 and 16 fully deployed and detached from the delivery apparatus.

DETAILED DESCRIPTION

Figure 1:
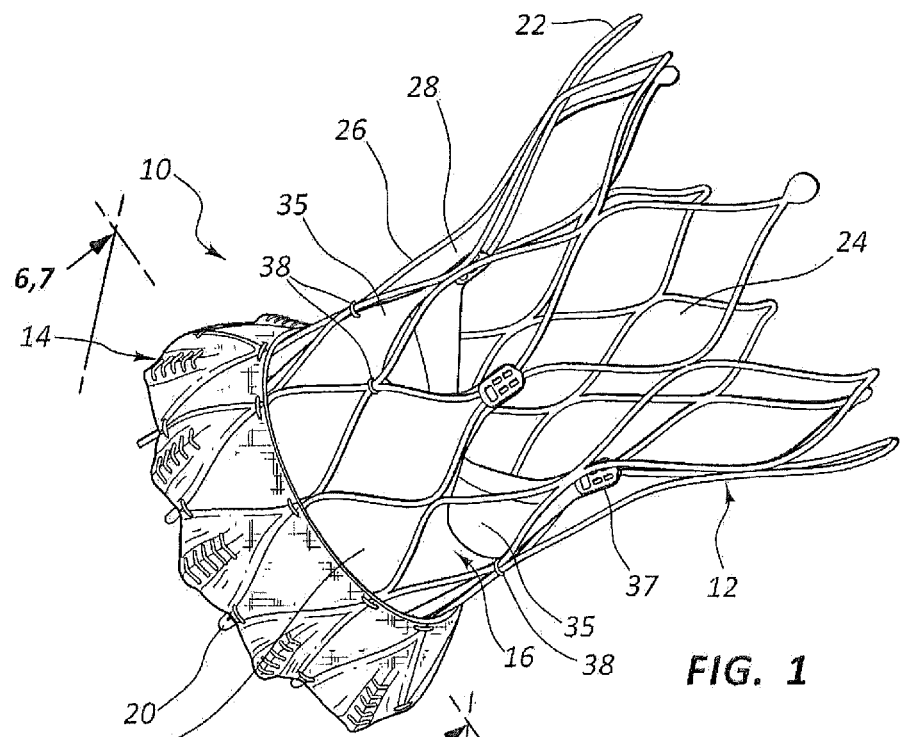
FIG. 1 is a perspective view of a heart valve assembly in accordance with the present disclosure.

The present disclosure relates to implantable heart valve assemblies having features that address paravalvular leak (PVL). PVL involves the flow of blood around the outside of the implantable heart valve assembly between the heart valve assembly and a native annulus within which the heart valve assembly is positioned. The native annulus may include the annulus of a native heart valve, which is being replaced by the implantable heart valve assembly. PVL typically occurs when the heart valve assembly is initially placed at the native annulus and insufficient time has elapsed for tissue in-growth through the stent of the heart valve assembly, which usually mitigates PVL. One object of the present disclosure is to create a seal between an exterior of the heart valve assembly and the native valve annulus upon implantation.

One aspect of the present disclosure relates to systems and methods for providing a sealing interface between the heart valve assembly and the native annulus at the implantation site. The sealing interface may include a sealing member. The sealing member may be separate from a valve member carried by the stent. The sealing member may be positioned around an outer perimeter surface of the stent. Alternatively, the sealing member may be positioned along an internal surface of the stent. The sealing member may include a plurality of protrusions that extend radially outward into contact with the native annulus. The protrusions may be referred to as puckers, tissue puckers, or folds, and may be formed in a radially outward facing surface of the sealing member. The protrusions may be arranged in a pattern. The protrusions may create a continuous sealing line or sealing interface with the native annulus to limit backflow of blood between the native annulus and an outer surface of the heart valve assembly. In an arrangement in which the sealing member is positioned along an internal surface of the stent, the protrusions may extend through cells or openings in the stent and into contact with the native annulus.

The need for a sealing member and associated sealing protrusions may arise from the use of a self-expanding stent of a self-expanding heart valve assembly. Self-expanding stents, as opposed to balloon inflated stents, may produce limited radially outward directed force against the native annulus. This limited radial force may create challenges in maintaining a seal between the stent and the native annulus without the use of a sealing member and/or associated sealing protrusions of the sealing member. A self-expanding stent may include regions that do not closely conform to the native annulus geometry due to unique shapes of the native valve. However, using a self-expanding stent may permit at least partially re-sheathing of the heart valve assembly to reposition the heart valve assembly relative to the native annulus during deployment.

The protrusions of the sealing member may fill gaps between the heart valve assembly and the native annulus which may otherwise provide flow paths that create PVL. The sealing protrusions may be compressible in other areas where the self-expanding stent has a close fit with the native annulus geometry.

The sealing member may be secured to the stent in a way that permits both deployment and re-sheathing of the heart valve assembly relative to a carrier tube used to deliver the heart valve assembly to the implantation site. For example, the sealing member may be connected to the stent at a plurality of locations along a length of the stent and around an outer peripheral surface of the stent to permit expansion and contraction of the stent without pinching or damaging the sealing member. In one example, the sealing member is connected to the stent with stitching at intersections between support struts of the stent (e.g., at an apex of one of the cells). The stitching may permit some relative movement between the stent and the sealing member.

Figure 2:
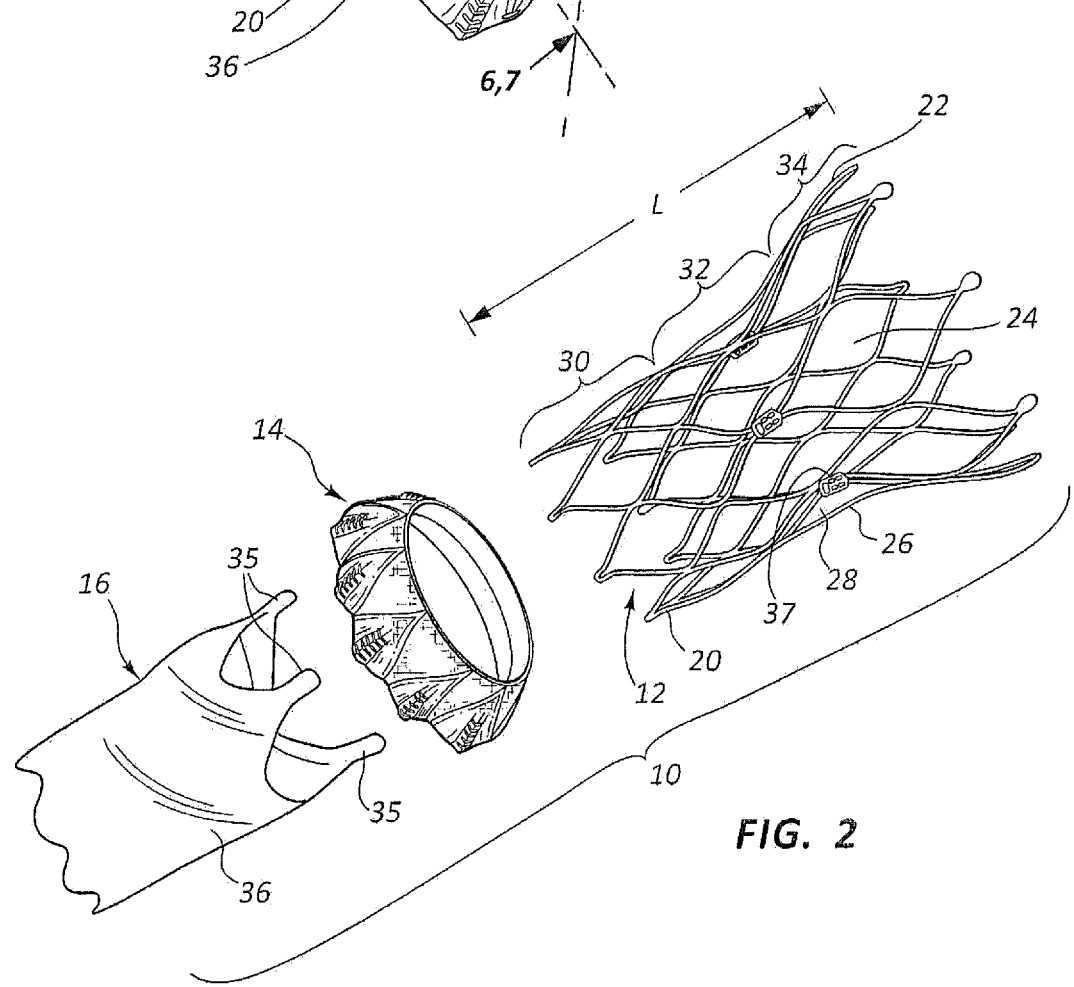
FIG. 2 is an exploded perspective view of the heart valve assembly of FIG. 1.

Referring now to FIGS. 1-2, an example heart valve assembly 10 is shown including stent 12, sealing member 14, and valve 16. Sealing member 14 is positioned on an exterior of stent 12 and extends around an outer periphery of stent 12. Valve 16 is positioned internally within stent 12. Heart valve assembly 10 may be positioned at an implantation site and may be used as a replacement valve for a native valve of the heart. Stent 12 may be a self-expandable and collapsible device and may be referred to as a self-expandable and collapsible stent.

Stent 12 may include inflow and outflow end portions 20, 22, interior 24, plurality of frame members 26 (also referred to as struts 26), and plurality of cells 28. Stent 12 may have several sections along its length including annular section 30, sinus section 32, and aortic section 34 (see FIG. 2). Aortic section 34 may be flared to a greater outer diameter than annular and sinus sections 30, 32. Annular, sinus and aortic sections 30, 32, 34 may provide different amounts of radially outward directed force at the implantation site, which may affect, for example, the sealing function of sealing member 14.

Sealing member 14 may provide an interface between a native annulus and stent 12 and/or valve 16. Sealing member 14 may provide an improved seal between the native annulus and heart valve assembly 10 that reduces PVL.

Valve 16 includes leaflets 35 and cuff 36. Cuff 36 typically extends distally to inflow end portion 20 of stent 12. Leaflets 35 may be connected to stent 12 with connecting members 37 (see FIG. 1). Connecting members 37 are typically positioned along sinus section 32 of stent 12. Cuff 36 may be connected to stent 12 at a plurality of locations along the length L and around a circumference of stent 12 using, for example, stitching 38 (see FIG. 1).

Figure 3:
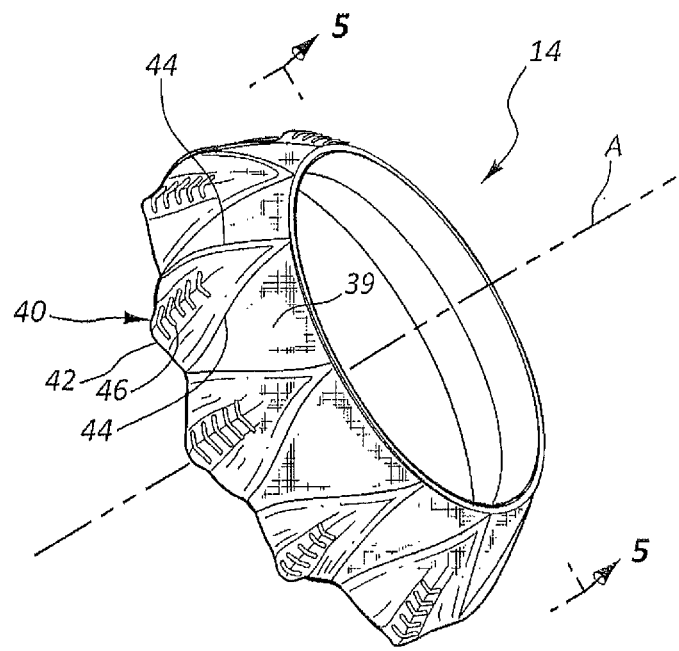
FIG. 3 is a perspective view of a sealing member of the heart valve assembly of FIG. 1.
Figure 4:
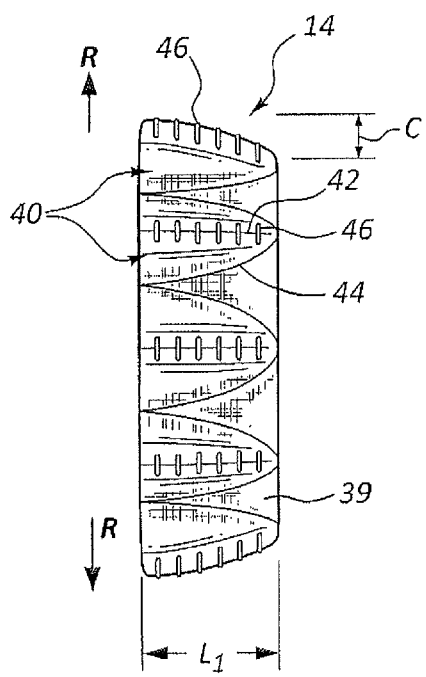
FIG. 4 is a side view of the sealing member of FIG. 3.
Figure 5:
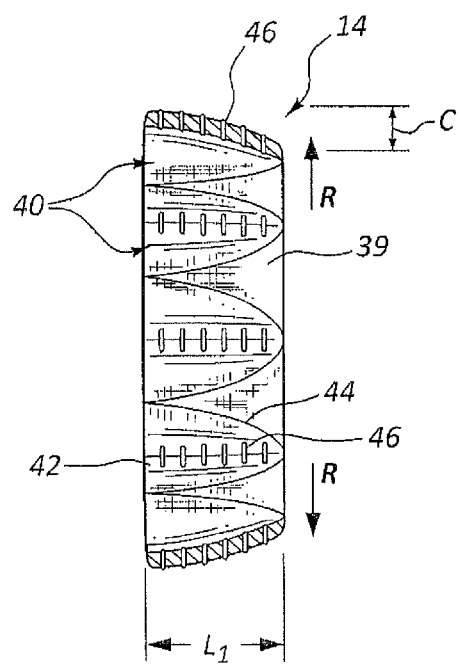
FIG. 5 is a cross-sectional view of the sealing member of FIG. 3 taken along cross-section indicators 5-5.

Sealing member 14 may be generally annular and include base 39 and plurality of protrusions 40, as shown in FIGS. 3-5. Each protrusion 40 includes center 42, perimeter 44, and stitching 46. Sealing member 14 is positioned extending around an outer circumferential surface of stent 12 when heart valve assembly 10 is assembled (see FIG. 1). Base 39 may have an inner surface that faces radially inward toward stent 12. Protrusions 40 extend radially outward away from base 39 and stent 12.

Each center 42 may extend centrally relative to perimeter 44. Center 42 may extend in a direction parallel with a longitudinal axis A of sealing member 14 (see FIG. 3). Perimeter 44 is typically in contact with stent 12 along base 39. Center 42 protrudes radially outward away from base 39. Protrusions 40 may have a diamond shape or half-diamond shape. Alternatively, each protrusion 40 may include or be referred to as a hemispherical, triangular, or conical shape.

Centers 42 define radially outward-most points along an exterior surface of sealing member 14. Centers 42 may include peak points relative to each protrusion 40 in a radially outward direction. Centers 42 may extend radially outward from perimeter 44 along base 39 a distance C (see FIGS. 4 and 5) in the range of about 0 mm to about 4 mm, and more particularly in the range of about 0 mm to about 1.5 mm. Distance C may be applicable to any of the protrusion embodiments disclosed herein.

Protrusions 40 may be referred to as puckers, puckering, or folds, which are formed in sealing member 14. Protrusions 40 may be formed by pinching, folding, gathering, or puckering portions of sealing member 14. The resulting radially outward protruding shape of protrusion 40 may be maintained using, for example, stitching 46. Stitching 46 is secured to material of protrusion 40 and may extend along center 42 and/or perimeter 44. Stitching 46 may define at least in part a shape and size of protrusion 40. For example, a location and shape of perimeter 44 may be determined by location and type of stitching 46 used.

Each center 42 may be deformable and compressible to conform to uneven surfaces of the native annulus to enhance a sealed interface between heart valve assembly 10 and the native annulus. The materials of sealing member 14, particularly those materials included in center 42, may provide deformable properties to center 42. For example, using a resilient, elastic material may permit a change of shape for protrusion 40 and particularly center 42. A shape and size of center 42 may provide deformability and compressibility of center 42 when pressed radially outward against the native annulus by stent 12.

Stitching 46 may assist in holding center 42 in a position protruding radially outward. Stitching 46 may be secured to protrusion 40 in a way that creates tension in center 42 to help maintain the pinched, puckered and/or folded configuration of protrusions 40. Stitching 46 may include, for example, a ladder stitch or a whip stitch.

Each perimeter 44 may provide a continuous sealing interface between heart valve assembly 10 and the native annulus that limits backflow of blood between the native annulus and heart valve assembly 10. Each center 42 and perimeter 44 individually or in combination with each other and/or base 39 may provide a cupping function against blood backflow, wherein center 42 and perimeter 44 of each protrusion 40 create a liquid-tight cupping or sealing interface between heart valve assembly 10 and the native annulus. Perimeter 44 may follow frame members 26. Perimeter 44 may be captured between frame members 26 and the native annulus as stent 12 applies a radially outward directed force to sealing member 14. Any portion of sealing member 14 captured between one of frame members 26 and the native annulus may provide a sealing point between heart valve assembly 10 and sealing member 14.

In other arrangements, perimeter 44 may be oriented on sealing member 14 at a location spaced away from frame members 26. Perimeter 44 may define a boundary between protrusions 40 and base 39 of sealing member 14. Protrusions 40 may begin to extend radially outward from the remaining portions of sealing member 14 at the boundary provided by perimeter 44.

Protrusions 40 may be positioned in series around an outer perimeter surface of sealing member 14 as shown in the side and cross-sectional views of sealing member 14 in FIGS. 4 and 5. Protrusions 40 may be positioned adjacent to each other and may be arranged side-by-side and in contact with each other. Protrusions 40 may be aligned linearly around an outer circumferential surface of base 39 of sealing member 14. Protrusions 40 may be arranged in a pattern of repeating shapes. Protrusions 40 may have the same size. Alternatively, protrusions 40 may have different shapes and sizes around a perimeter of sealing member 14.

Sealing member 14 has a length $L_1$ as shown in FIGS. 4 and 5. Length $L_1$ may be less than a length of any one of annular, sinus and aortic sections 30, 32, 34 of stent 12. At its greatest length, length $L_1$ is less than length L of stent 12 (see FIG. 2). Length $L_1$ is typically great enough to provide overlapping with at least a portion of valve 16 when sealing member 14 is positioned at any location along length L of stent 12.

The portion of sealing member 14 that overlaps with valve 16 may be connected to valve 16 either directly or indirectly. Sealing member 14 and valve 16 may be directly connected together using, for example, fasteners, stitching, or a bonding agent.

Protrusions 40 may coincide with the shape and size of cells 28, or a portion of cells 28 of stent 12 (see FIGS. 1 and 2). Protrusions 40, including perimeters 44 of protrusions 40, may have a shape that substantially matches the horseshoe-shaped, half cells 28 (also referred to as half diamond shaped portions) along inflow end portion 20 of stent 12. In at least some arrangements, protrusions 40 are axially spaced from inflow end portion 20 such that sealing member 14 may have a shape that matches an entire cell 28 of stent 12. Sealing member 14 may be arranged on stent 12 at a location to provide alignment with the native annulus at the implantation site.

Figure 6:
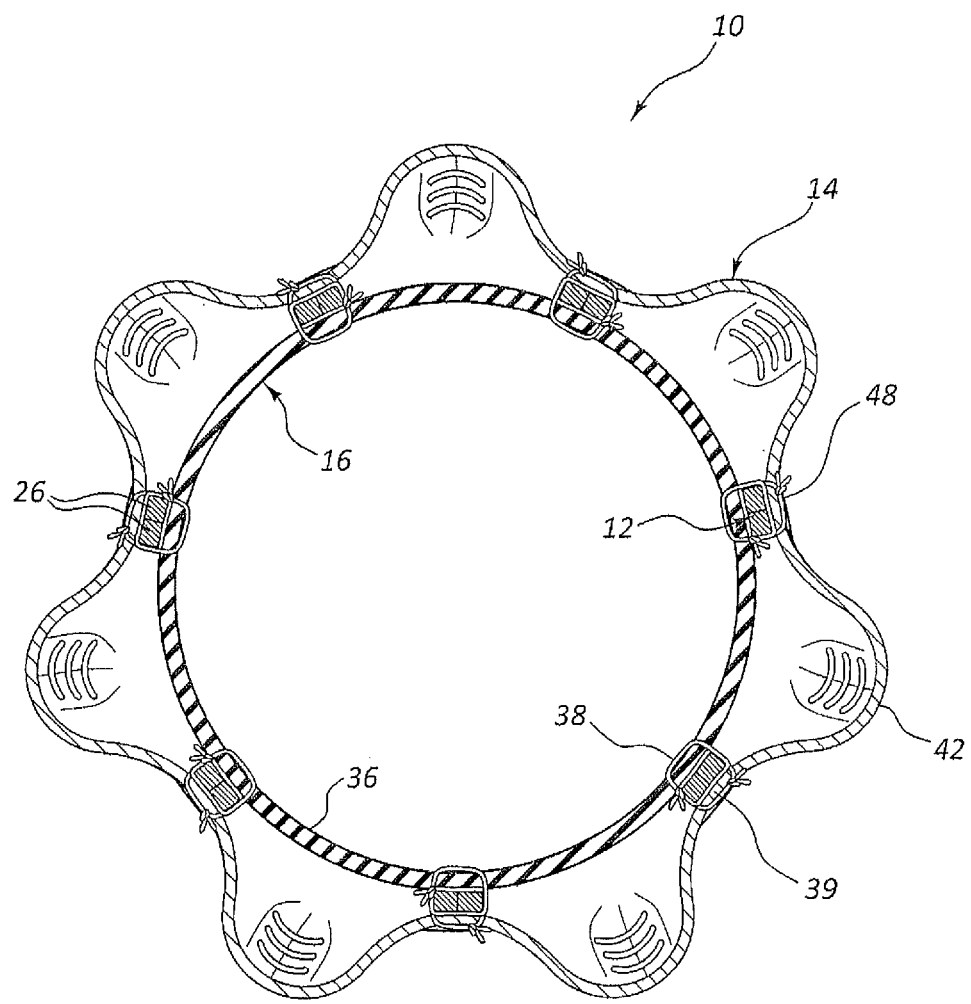
FIG. 6 is a cross-sectional view of the heart valve assembly of FIG. 1 taken along cross-section indicators 6-6 with a first suture connection arrangement.

Sealing member 14 may be connected to stent 12 using any suitable attachment method. For example, sealing member 14 of heart valve assembly 10 may be connected to stent 12 using stitching 48, as shown in FIG. 6. Stitching 48 may extend around or adjacent to portions of frame members 26 and extend through base 39 of sealing member 14. FIG. 6 shows stitching 48 extending only through sealing member 14 and wrapping around portions of frame members 26. Separate stitching 38 extends through cuff 36 of valve 16 and wraps around portions of frame members 26 to secure valve 16 to stent 12. Stitching 38 and attachment stitching 48 may be positioned axially adjacent to each other. The stitching arrangement of FIG. 6 may be helpful when connecting sealing member 14 to stent 12 in a separate assembly step from connecting valve 16 to stent 12. For example, valve 16 may be mounted to stent 12 with stitching 38 followed by mounting sealing member 14 to stent 12 with stitching 48. Stitching 48 may be positioned at any location along frame members 26 such as at intersection points of frame members 26.

Figure 7:
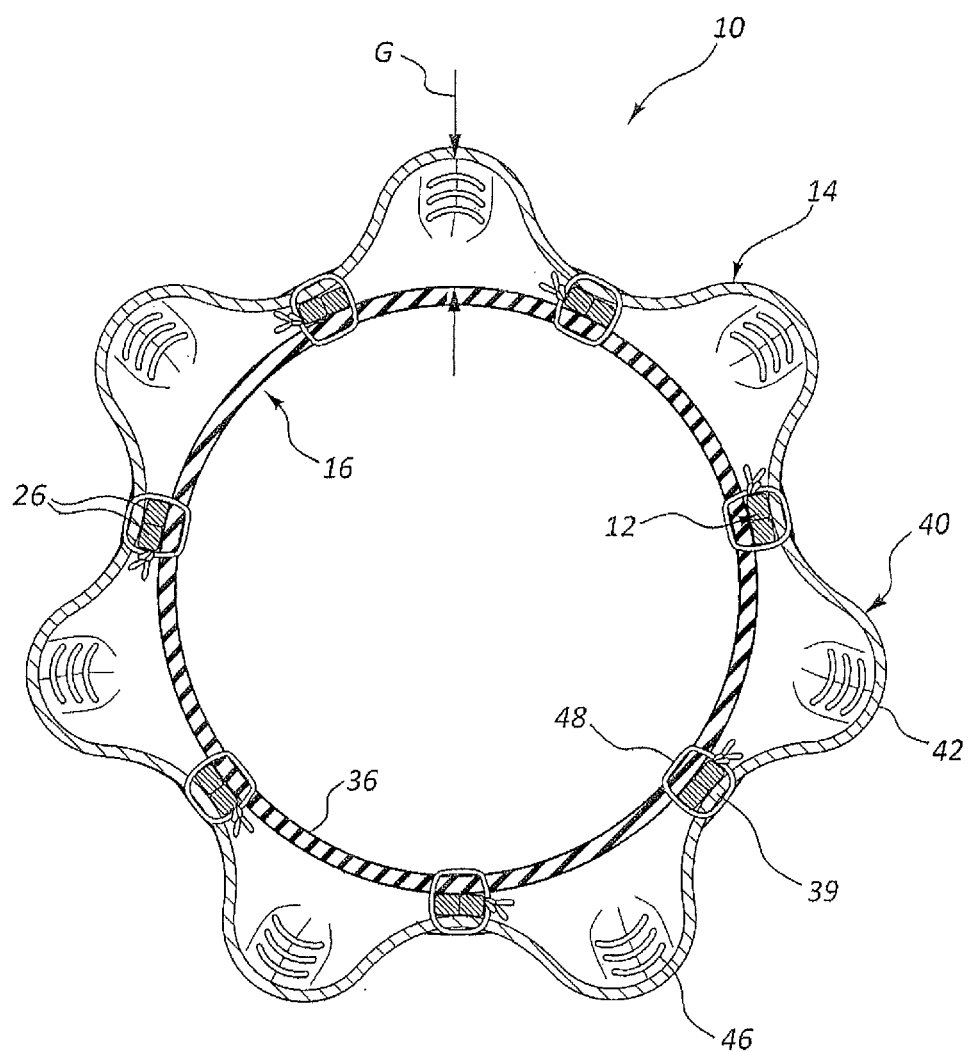
FIG. 7 is a cross-sectional view of the heart valve assembly of FIG. 1 taken along cross-section indicators 7-7 with an alternative second suture connection arrangement.

FIG. 7 shows stitching 48 extending through cuff 36 of valve 16, around portions of frame members 26, and through base 39 of sealing member 14. Stitching 48 may extend along a portion of two separate frame members 26, as shown in FIG. 7. Stitching 48 may extend through each of sealing member 14 and valve 16 at two separate locations. The arrangement of FIG. 7 includes a single stitching 48 connecting sealing member 14 and valve 16 together and connecting sealing member 14 and valve 16 to stent 12.

As shown in FIG. 7, a gap G exists between center 42 of protrusion 40 and valve 16. Gap G provides a space into which center 42 may deform radially inwardly when sealing member 14 is pressed against the geometry of the native annulus. Center 42 may elastically deform into gap G and return to the rest position shown in FIG. 7 after being removed from contact with the native annulus. Stitching 48 holds base 39 of sealing member 14 secured to stent 12 while center 42 deforms into gap G.

Figure 8:
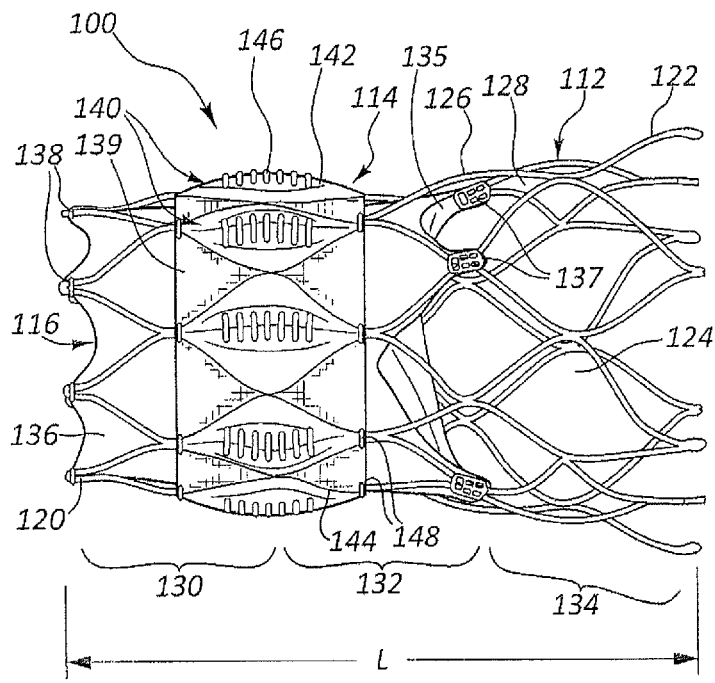
FIG. 8 is a side view of another heart valve assembly in accordance with the present disclosure.

FIG. 8 shows heart valve assembly 100 having stent 112, sealing member 114, and valve 116. Stent 112 includes inflow and outflow end portions 120, 122, interior 124, frame members 126, cells 128, and annular, sinus and aortic sections 130, 132, 134. Valve 116 includes leaflets 135 and cuff 136. Leaflets 135 of valve 116 may be connected to stent 112 with connecting members 137. Connecting members 137 are typically positioned along sinus section 132 of stent 112. Cuff 136 of valve 116 may be connected to stent 112 with stitching 138.

Sealing member 114 includes base 139 and plurality of protrusions 140. Each protrusion 140 includes center 142, perimeter 144, and stitching 146 (see FIG. 9). Each protrusion 140 has a generally diamond-shaped perimeter 144. Each protrusion 140 may have a shape that generally matches a shape of cell 128 of stent 112 aligned with protrusion 140, as shown in FIG. 8. Perimeter 144 of each protrusion 140 may track along frame members 126 of stent 112 that are covered by sealing member 114. Sealing member 114 may be connected to frame members 126 along perimeter 144 of at least some of protrusions 140 using, for example, stitching 148. Center 142 may extend longitudinally between axially spaced apart apexes of cells 128.

Figure 9:
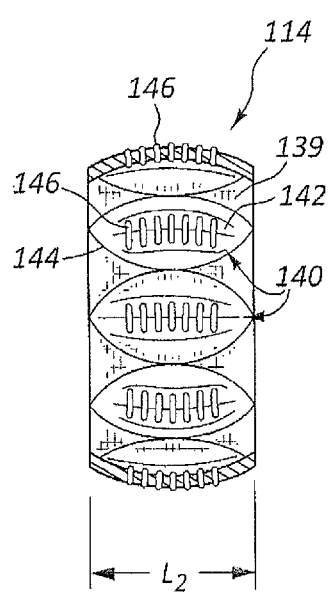
FIG. 9 is a cross-sectional view of a sealing member of the heart valve assembly of FIG. 8.

Protrusions 140 may have a contoured, generally dome-shaped construction, as shown in the cross-sectional view of FIG. 9. Stitching 146 may extend along center 142 and apply tension in material of sealing member 14 that holds center 142 extending radially outward relative to perimeter 144 and/or base 139. Stitching 146 may include, for example, a ladder stitch or a whip stitch.

Sealing member 114 typically overlaps at least a portion of valve 116, as shown in FIG. 8. Sealing member 114 may be positioned directly adjacent to one of the ends of valve 116. Typically, sealing member 114 is positioned distal (e.g., toward the heart and away from the operator) of leaflets 135 of valve 116 and overlapping cuff 136 to provide improved sealing between the native annulus and valve 116.

Sealing member 114 may be connected to stent 112 using, for example, stitching, adhesives, or fasteners. In one example, attachment stitching 148 may be used to connect sealing member 114 to frame members 126 of stent 112. In at least some examples, attachment stitching 148 may be positioned at the intersection of frame members 126. Attachment stitching 148 may be able to slide along frame members 126 to permit some relative movement between sealing member 114 and stent 112 during expansion and collapsing of stent 112. Cuff 136 of valve 116 may also be connected to stent 112 using attachment stitching 148. Attachment stitching 148 may be used to connect sealing member 114 to stent 112, valve 116 to stent 112, and sealing member 114 to valve 116.

Sealing member 114 has a length $L_2$, as shown in FIG. 9. Length $L_2$ may be substantially the same length as a length of cells 28 along that portion of stent 112 overlapped by sealing member 114. Length $L_2$ may be less than a length of any one of annular, sinus and aortic sections 130, 132, 134 of stent 112. Length $L_2$ typically is less than half of length L of stent 112 (see FIG. 8).

Figure 10:
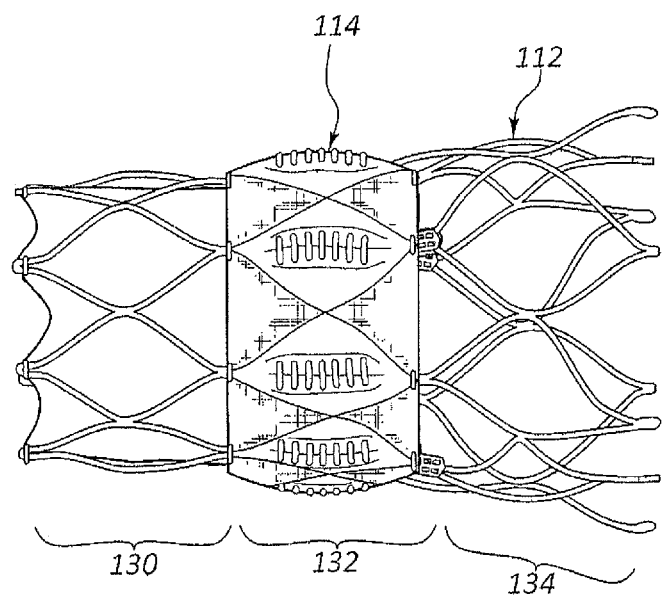
FIG. 10 is a side view of the heart valve assembly of FIG. 8 with the sealing member positioned at a different axial position.

Sealing member 114 may be positioned at other axial positions along length L of stent 112, such as the position shown in FIG. 10. FIG. 10 shows an embodiment similar to FIG. 8, the details of which will not be repeated for the sake of brevity. FIG. 10 shows sealing member 114 positioned primarily within sinus section 132 of stent 112 rather than overlapping annular and sinus sections 130, 132 as in the arrangement of FIG. 8. In other embodiments, sealing member 114 may at least partially overlap multiple sections 130, 132, 134, such as partially overlapping aortic section 134 in addition to annular section 130 and/or sinus section 132.

Figure 11:
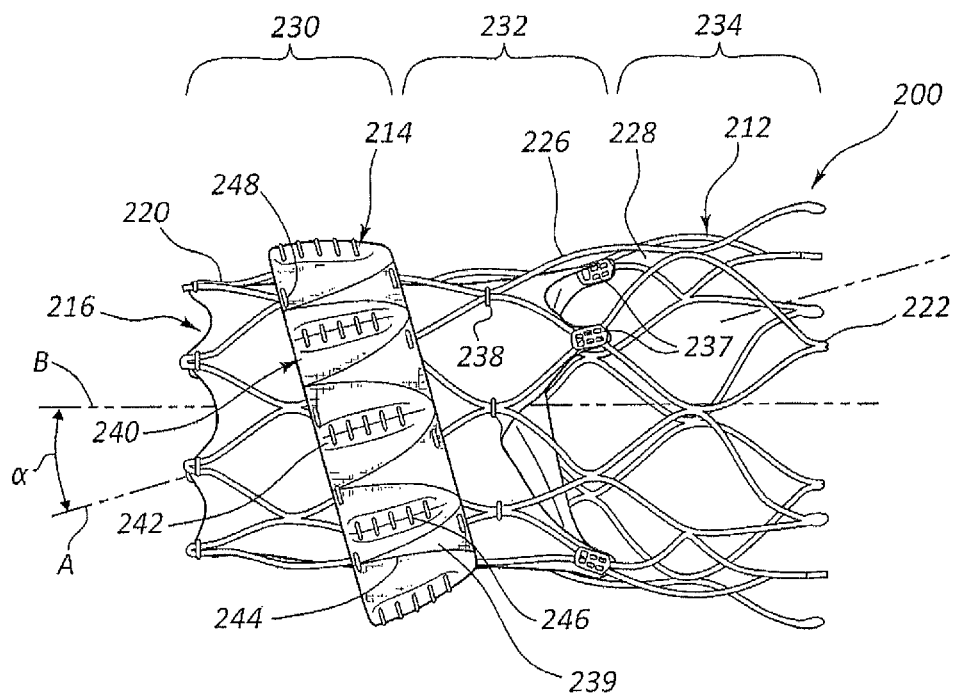
FIG. 11 is a side view of another heart valve assembly with a sealing member arranged at an angle.

FIG. 11 shows heart valve assembly 200 having stent 212, sealing member 214, and valve 216. Stent 212 includes inflow and outflow end portions 220, 222, plurality of frame members 226 that define plurality of cells 228, and annular, sinus and aortic sections 230, 232 and 234. Valve 216 may be connected to stent 212 with connecting members 237 and stitching 238. Connecting members 237 are typically positioned along sinus section 232 of stent 212.

Central axis A of sealing member 214 may be arranged at angle α relative to longitudinal axis B of stent 212 rather than being coaxial with longitudinal axis B (as compared to the coaxial arrangements of FIGS. 1-10). Angle α is typically in the range of about 0° to about 45°, and more particularly in the range of about 10° to about 30°.

Sealing member 214 may span or extend across multiple sections of stent 212, such as annular section 230 and sinus section 232, or sinus section 232 and aortic section 234. Alternatively, sealing member 214 may be positioned within only one of annular, sinus and aortic sections 230, 232, 234.

Sealing member 214 includes base 239 and a plurality of protrusions 240. Protrusions 240 each include center 242, perimeter 244, and stitching 246. At least some of protrusions 240 may overlap portions of multiple cells 228 of stent 212.

The angled arrangement of sealing member 214 may address challenges associated with off-axis arrangements of the native annulus that result from, for example, off-axis arrangement of the aorta relative to the heart. For example, if the aorta is arranged at an angle α from a central axis of the annulus, sealing member 214 may also be positioned at an angle α relative to stent 212 to provide better alignment of sealing member 214 with the native annulus.

Sealing member 214 may be connected to stent 212 using, for example, attachment stitching 248. In at least some examples, attachment stitching 248 may be connected to stent 212 at the intersection of frame members 226. Attachment stitching 248 may be able to slide along at least some of frame members 226 to permit some relative movement between sealing member 214 and stent 212 during expansion and collapsing of stent 212 while still maintaining the angled orientation of sealing member 214.

Figure 12:
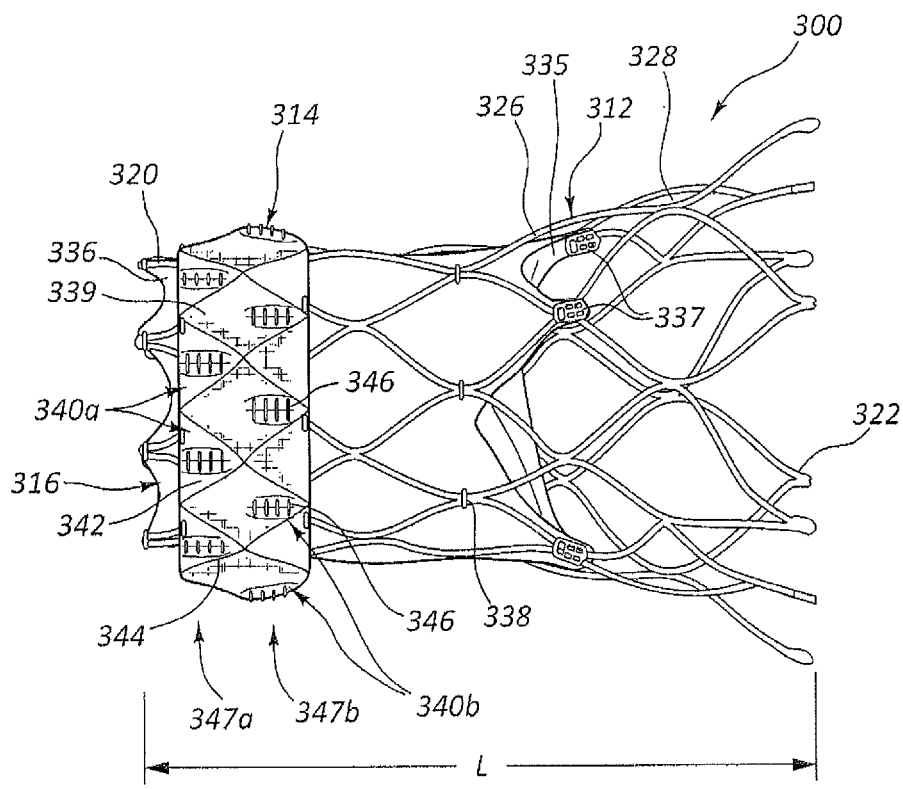
FIG. 12 is a side view of another heart valve assembly with a sealing member having two rows of sealing protrusions.

FIG. 12 shows heart valve assembly 300 having stent 312, sealing member 314, and valve 316. Stent 312 includes inflow and outflow end portions 320, 322 and plurality of frame members 326 that define a plurality of cells 328. Valve 316 includes leaflets 335 and cuff 336. Leaflets 335 may be connected to stent 312 with connecting members 337. Cuff 336 of valve 316 may be connected to stent 312 with stitching 338.

Sealing member 314 includes base 339 and plurality of protrusions 340a, 340b. Each of protrusions 340a, 340b includes center 342, perimeter 344, and stitching 346. Protrusions 340a, 340b may be arranged in first and second rows 347a, 347b, respectively. First and second rows 347a, 347b are arranged axially in series and directly adjacent to each other along a length of sealing member 314. First row 347a may be positioned adjacent to or closest to inflow end portion 320.

Protrusions 340a in first row 347a are circumferentially offset relative to protrusions 340b in second row 347b. Protrusions 340a may be arranged out of axial alignment with protrusions 340b in an axial direction. Protrusions 340a, 340b may create a diamond pattern. Perimeters 344 may be aligned with frame members 326 of stent 312 such that centers 342 are overlapping cells 328. Protrusions 340a, 340b may have a half diamond or half cell shape defined in part by perimeter 344. The shape of protrusions 340a, 340b may be referred to as a horseshoe shape.

Protrusions 340a, 340b and their associated centers 342 and perimeters 344 may provide multiple rows of sealing interfaces between sealing member 314 and the native annulus. Each row 347a, 347b of protrusions 340a, 340b may provide a separate sealing interface or plurality of sealing interfaces with the native annulus to limit PVL. Other embodiments are possible in which sealing member 314 includes three or more rows of protrusions, wherein each row of protrusions includes a plurality of individual protrusions. The protrusions of adjacent rows may be offset circumferentially. Protrusions 340a, 340b may have any shape and size to provide a desired number and arrangement of protrusions on a given sealing member.

Figure 13:
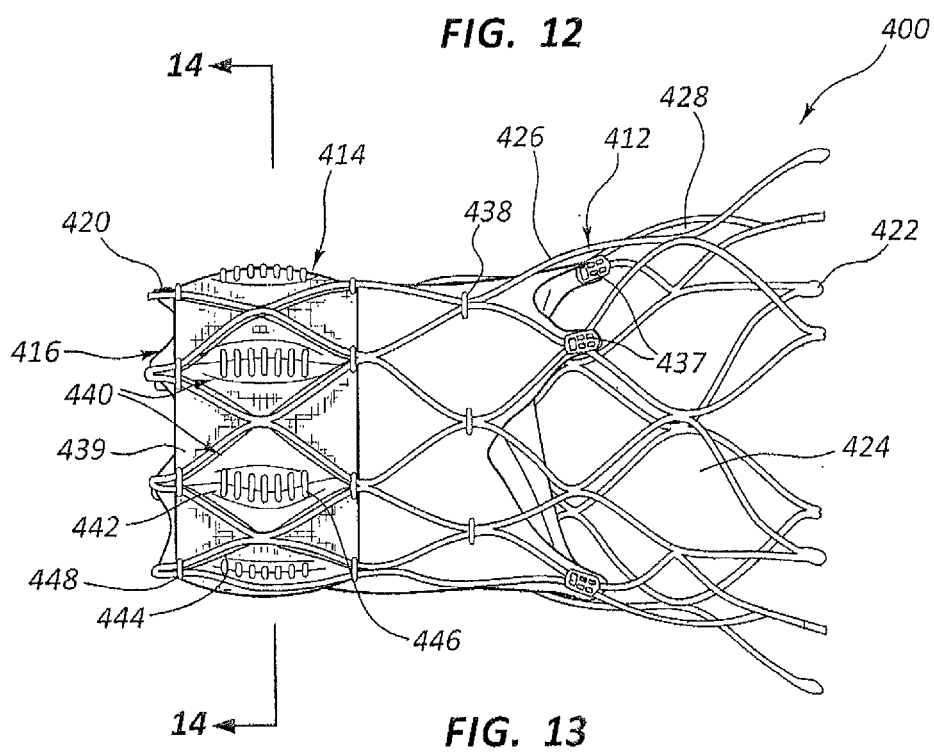
FIG. 13 is a side view of another heart valve assembly with a sealing member protruding through cells of a stent.

FIG. 13 shows heart valve assembly 400 having stent 412, sealing member 414, and valve 416. Stent 412 includes inflow and outflow end portions 420, 422, interior 424, plurality of frame members 426, and plurality of cells 428. Valve 416 may be connected to stent 412 with connecting members 437. Valve 416 may also be connected to stent 412 with stitching 438.

Sealing member 414 includes base 439 and plurality of protrusions 440. Protrusions 440 each include center 442, perimeter 444, and stitching 446. Base 439 of sealing member 414 is positioned within interior 424 and arranged in contact with an interior surface of stent 412. Protrusions 440 extend radially outward through cells 428 to a location outside of stent 412. Sealing member 414 may be positioned entirely within stent 412 prior to deployment at an implantation site. Protrusions 440, or at least portions thereof, may automatically extend radially outward through cells 428 when heart valve assembly 400 is deployed at the implantation site.

Figure 14:
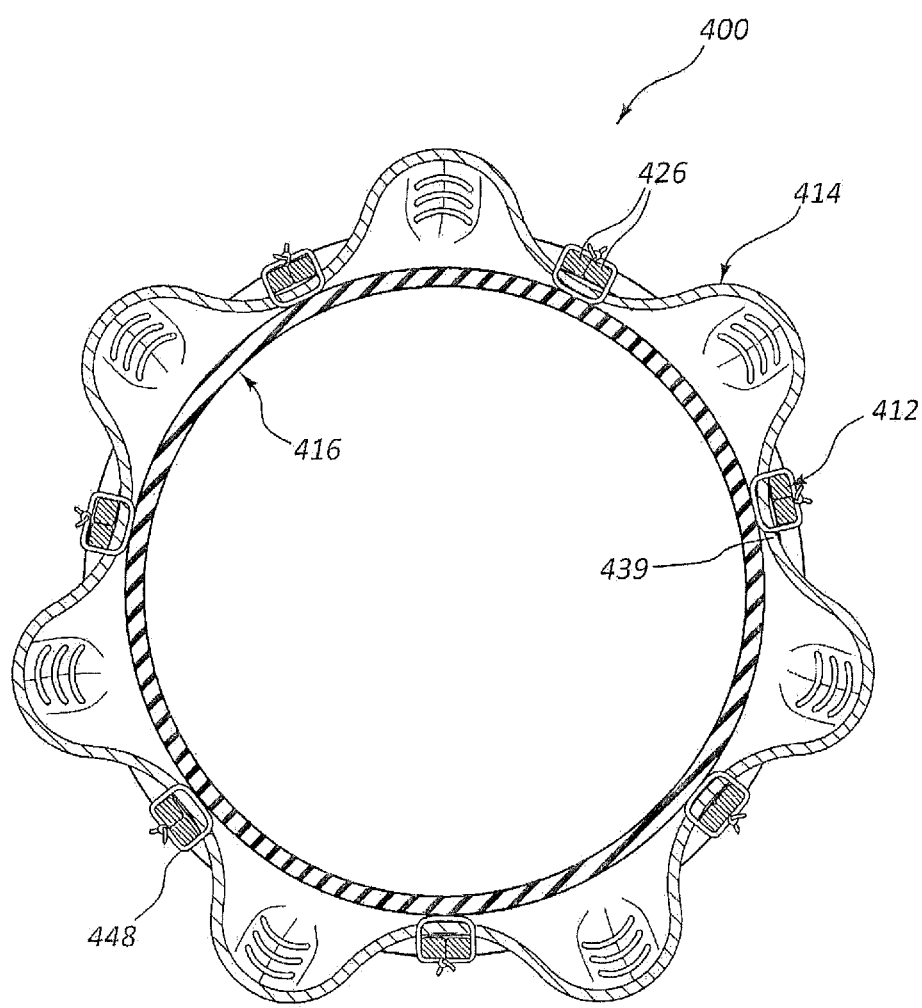
FIG. 14 is a cross-sectional view of the heart valve assembly of FIG. 13 taken along cross-section indicators 14-14.

Sealing member 414 may be interposed between stent 412 and a portion of valve 416. At least portions of sealing member 414 (e.g., base 439) may be positioned overlapping with valve 416. Base 439 of sealing member 414 is shown in FIG. 14 arranged in contact with an inner surface of stent 412. An inner surface of sealing member 414 (e.g., an inner surface of base 439) may be arranged in contact with an outward facing surface of valve 416.

Sealing member 414 and valve 416 may be directly connected together. Sealing member 414 and valve 416 may be connected to stent 412 at a plurality of common attachment locations. Alternatively, sealing member 414 may be connected to stent 412 at different locations than where valve 416 is connected to stent 412.

Sealing member 414 may be secured to stent 412 using plurality of attachment stitches 448, as shown in FIG. 13 and the cross-sectional view of FIG. 14. Attachment stitches 448 may connect sealing member 414 to frame members 426 of stent 412, as shown in FIG. 14. Attachment stitches 448 may extend through both sealing member 414 and valve 416 to provide a connection there between. In alternative embodiments, the same attachment stitches 448 used to secure sealing member 414 and valve 416 together may also wrap around portions of stent 412 to provide a connection with stent 412.

FIG. 14 shows base 439 of sealing member 414 interposed between interior surfaces of frame members 426 and an exterior surface of valve 416. Stent 412 may radially expand sealing member 414 and valve 416 by applying a pulling force in a radial outward direction when stent 412 is deployed rather than pushing sealing member 414 radially outward as in other embodiments in which the sealing member is positioned entirely outside of stent 412. When stent 412 is collapsed (e.g., re-sheathed), stent 412 pushes sealing member 414 and valve 416 radially inward to collapse sealing member 414 and valve 416. The pulling and pushing forces applied by stent 412 to sealing member 414 during expansion and collapsing, respectively, is opposite to the forces applied by stent 12 to sealing member 14 described above related to heart valve assembly 10. That is, stent 12 pushes sealing member 14 during expansion and pulls sealing member 14 during collapsing.

In alternative embodiments (not shown), the sealing member may include only a number of protrusions that matches the number of leaflets of the valve. Typically, an area around the valve assembly where greatest PVL occurs is adjacent to the leaflets of the valve because of the high level of movement of the valve in that location and the associated tension applied to the stent by the moving leaflets. Positioning a protrusion directly adjacent to the leaflets of the valve in either a radially outward direction or distal direction may address many of the potential PVL issues for a valve assembly. In one arrangement in which the valve includes three leaflets, the sealing member includes only three protrusions with each protrusion positioned in a cell of the stent just distally of the leaflets.

FIGS. 15-18 show heart valve assembly 10 in combination with delivery system 50. Delivery system 50 is shown in FIGS. 15 and 16 including carrier tube 52, deployment member 54, and tip 56. Carrier tube 52 includes interior 58 for containing heart valve assembly 10 during delivery to the implantation site (see FIG. 16). FIGS. 15-18 show heart valve assembly 10 at various stages of deployment relative to delivery system 50. FIGS. 15 and 16 show heart valve assembly 10 compressed, collapsed and completely enclosed in carrier tube 52 prior to deployment. FIG. 17 shows heart valve assembly 10 partially deployed. FIG. 18 shows heart valve assembly 10 fully deployed and disconnected from delivery system 50.

Prior to deployment, heart valve assembly 10 is collapsed or compressed and positioned entirely within carrier tube 52, as shown in FIGS. 15 and 16. Sealing member 14 may overlap portions of stent 12 and valve 16 when heart valve assembly 10 is compressed and held within carrier tube 52, as shown in FIG. 16. Sealing member 14 may be positioned between portions of stent 12 and/or valve 16 and an internal surface of interior 58 of carrier tube 52. Deployment member 54 is connected to outflow end portion 22 of stent 12. Tip 56 extends through heart valve assembly 10 and provides a tapered leading end for improved navigation through vessels to the implantation site.

Deploying heart valve assembly 10 is initiated by retracting carrier tube 52 in proximal direction P (relative to the operator), as shown in FIG. 17. Carrier tube 52 may be incrementally withdrawn in proximal direction P and advanced in distal direction D to provide various stages of partial deployment of heart valve assembly 10. A partial deployment of heart valve assembly 10 includes any exposure of heart valve assembly 10 outside of carrier tube 52 while maintaining connection of deployment member 54 to outflow end portion 22 of stent 12. FIG. 17 shows stent 12 fully deployed from carrier tube 52 while remaining connected to deployment member 54. Heart valve assembly 10 may be re-sheathed, or at least partially re-sheathed, back into carrier tube 52 from any full or partial deployment of heart valve assembly 10. Re-sheathing is done by advancing carrier tube 52 relative to heart valve assembly 10 in distal direction D.

Stent 12, sealing member 14 and valve 16 typically self-expand into an expanded, deployed position after being released from the constraining force applied by carrier tube 52. Sealing member 14 extends around an outer peripheral surface of stent 12 when heart valve assembly 10 moves into the expanded, partially deployed position of FIG. 17. Protrusions 40 of sealing member 14 create a sealed interface between heart valve assembly 10 and the native annulus (e.g., see FIG. 19).

FIG. 18 shows deployment member 54 disconnected from stent 12 so that heart valve assembly 10 is fully deployed. Deployment member 54 may include a plurality of actuatable fasteners or other connection features that permit selective disconnection from stent 12. Once disconnected from deployment member 54, outflow end portion 22 of stent 12 further expands radially outward.

Figure 19:
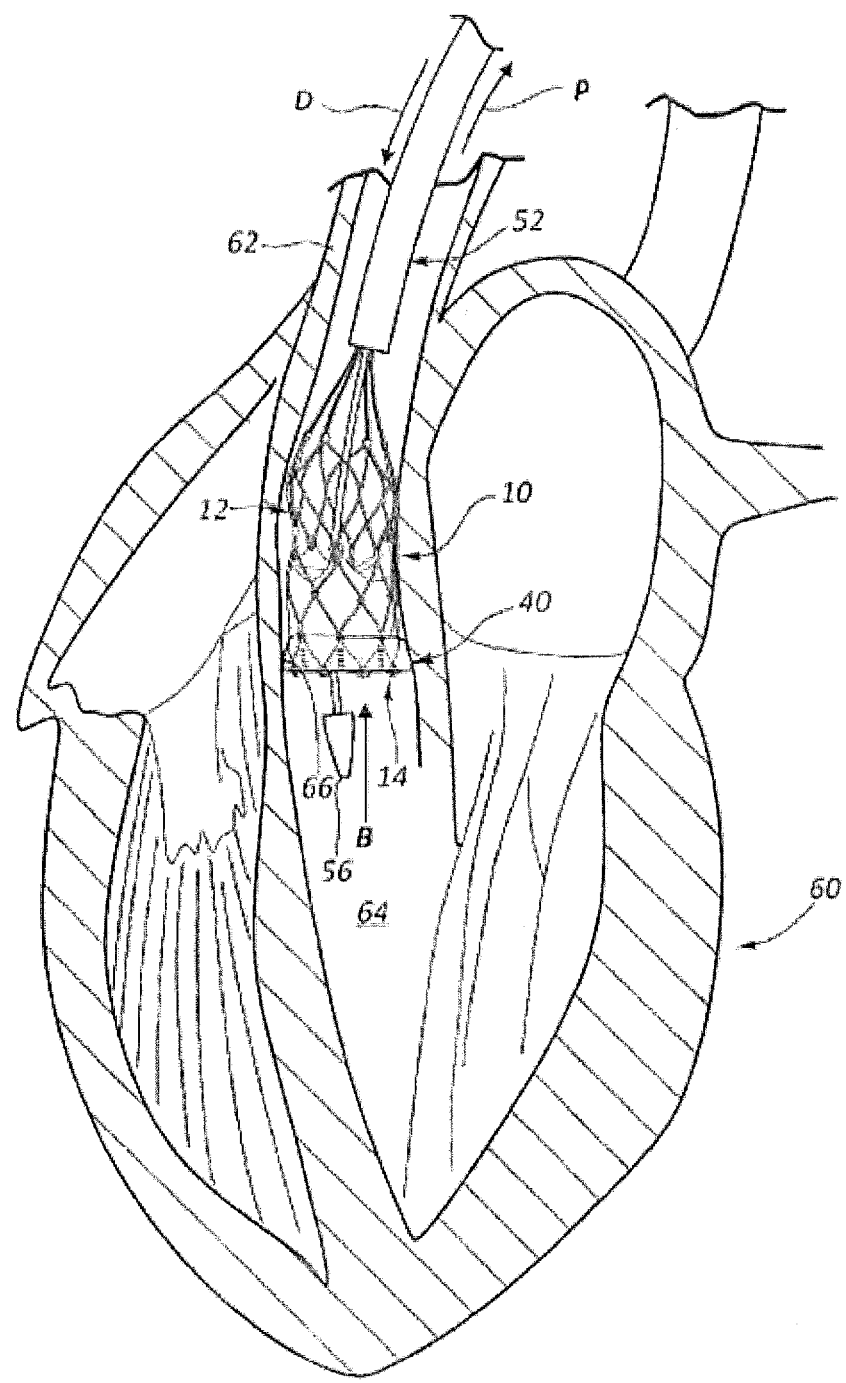
FIG. 19 shows the heart valve assembly of FIG. 1 partially deployed at a native annulus of a heart.
Figure 20:
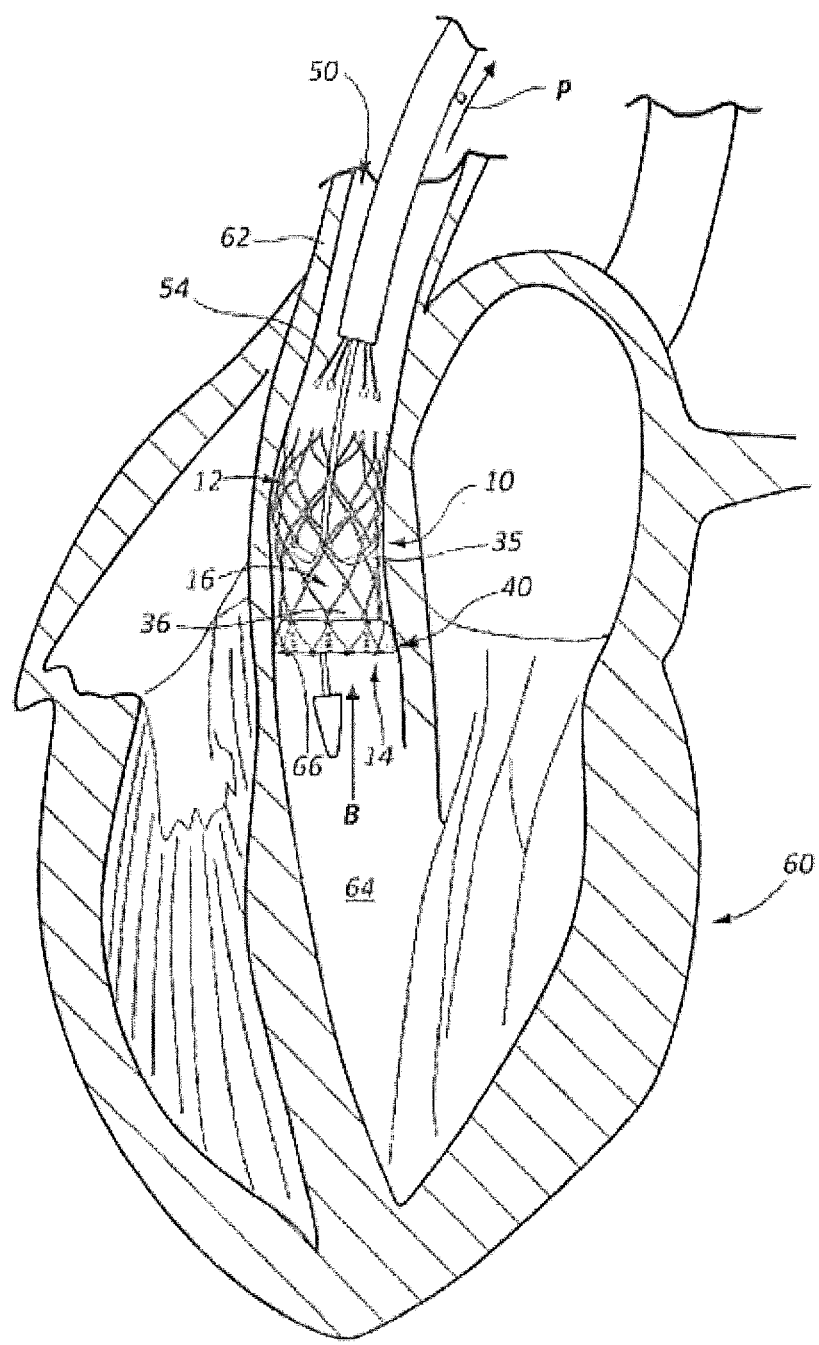
FIG. 20 shows the heart valve assembly of FIG. 1 fully deployed at a native annulus of a heart.

FIGS. 19 and 20 show heart valve assembly 10 and delivery system 50 positioned within heart 60. Heart 60 is shown in FIGS. 19 and 20 including aorta 62, left ventricle 64, and native annulus 66. Blood flow B is in a direction out of left ventricle 64 and into aorta 62 when heart 60 pumps. Blood attempts to flow in an opposite direction back into left ventricle 64 from aorta 62 when heart 60 relaxes.

Heart valve assembly 10 is initially deployed at native annulus 66 by positioning tip 56 through native annulus 66 and aligning sealing member 14 of heart valve assembly 10 with native annulus 66. Heart valve assembly 10 is partially deployed at native annulus 66 by withdrawing carrier tube 52 is proximal direction P, as shown in FIG. 19. Stent 12 expands radially outward to press protrusions and 40 sealing member 14 against native annulus 66 to form a seal therebetween. The operator may test for PVL by injecting a contrast agent in the area of heart valve assembly 10.

The operator may choose to reposition heart valve assembly 10 to address PVL issues observed using the ejected contrast agent. Re-sheathing is initiated by advancing carrier tube 52 in distal direction D. Typically, the operator at least partially re-sheaths heart valve assembly 10 enough to relieve the radially outward force applied by heart valve assembly 10 to native annulus 66. The operator then axially and/or rotationally repositions heart valve assembly 10 relative to native annulus 66. Heart valve assembly 10 is again partially redeployed by retracting carrier tube 52. Contrast agent is again ejected at native annulus 66 to test for PVL. If needed, the operator may again at least partially re-sheath and then reposition heart valve assembly 10 relative to native annulus 66 followed by ejecting contrast agent to test for PVL.

Once the operator is satisfied with the position of heart valve assembly 10 at native annulus 66 of heart 60, the operator may detach deployment member 54 from stent 12 to completely deploy heart valve assembly 10 at native annulus 66 by detaching stent 12 from deployment member 54, as shown in FIG. 20. Delivery system 50 is then withdrawn in direction P from the patient.

With heart valve assembly 10 completely deployed at native annulus 66, heart valve assembly 10 may operate to control blood flow between left ventricle 64 into aorta 62 and sealing member 14 provides resistance to PVL. Leaflets 35 of valve 16 may open in response to pressurized flow of blood out of left ventricle 64 and into aorta 62. Leaflets 35 close after the pressurized flow of blood from left ventricle 64 stops to prevent back flow of blood from aorta 62 into left ventricle 64. Sealing member 14 (e.g., protrusions 40) is pressed against native annulus 66 by stent 12 to create a seal that limits backflow of blood from aorta 62, around an outer perimeter of heart valve assembly 10, and into left ventricle 64. Sealing member 14 may provide a sealed interface between an outer surface of valve 16 (e.g., outer surface of valve cuff 36) and native annulus 66 that limits PVL.

The sealing members disclosed herein may comprise various materials. The material of the sealing member may generally be referred to as tissue. The sealing member may comprise, for example, a fabric such as Polytetrafluoroethylene (PTFE), Dacron, or Polyvinyl alcohol (PVA) threads, or other materials such as Gor-tex® and polymers such as silicone, saline, PVA, plastics, or living tissue such as fat. The sealing member may include an inflatable material or have an inflatable construction configured to hold a volume of inflation fluid (e.g., liquid saline or a gas). The sealing member may be inflatable after the heart valve assembly is deployed at an implantation site. The sealing member may be deflatable prior to being re-sheathed as part of repositioning the heart valve assembly relative to an annulus. The sealing member may include multiple materials. Further, some features of the sealing member, such as the protrusions, may have different materials from other portions of the sealing member. For example, the sealing member may comprise a base layer comprising a first material, and the protrusions may extend radially outward from the base layer and comprise a second material.

A number of methods may be associated with the heart valve assemblies and sealing members disclosed herein. One example method relates to a method of forming a sealing member. The method includes pinching or folding portions of the sealing member at a plurality of locations around a perimeter of the sealing member, and fixing the folded or pinched portion to provide a plurality of protrusions extending radially outward from the sealing member. The protrusions may be fixed using stitching. The stitching may extend around a perimeter of each of the protrusions. The stitching may extend along a center line of the protrusions. The stitching may include, for example, a ladder stitch, a whip stitch, reverse running stitches, or a crossing stitch that helps fix a bulged shape for the protrusion. The protrusions may be contoured and include a cup shape, such as a hemispherical shape. Many other shapes and various sizes are possible for the protrusion. The sealing member may have any arrangement or pattern of protrusions around its periphery. Depending on the type of material used in the sealing member, the protrusions alternatively may be heat set or formed using a particular knitting pattern or material density in the sealing member.

Another example method relates to manufacturing a valve assembly. The method may include providing a stent, a valve, and a sealing member, wherein the stent has a self-expandable and collapsible construction and the sealing member includes a plurality of protrusions. The valve may be mounted within the stent. The sealing member may be mounted to the stent with the plurality of protrusions extending radially outward. The protrusions may extend through cells (e.g., between frame members) of the stent. The sealing member may be positioned on an exterior surface of the stent, or may be positioned along an interior surface of the stent with the protrusions extending through the stent. The sealing member may overlap a portion of the valve, such as a base portion of the valve spaced axially from leaflets of the valve. A plurality of protrusions may be arranged in rows or other patterns around an outer periphery surface of the sealing member. The sealing member may be secured to the stent using, for example, stitching or other attachment means. The sealing member may be connected to the stent in a way that permits self-expanding and collapsing of the stent, which occurs during placement and repositioning of the heart valve assembly at an implantation site.

Another method relates to deploying a heart valve assembly at an implantation site such as at the site of a native heart valve. The method may include providing the heart valve assembly with a stent, a valve, and a sealing member. The sealing member may include a plurality of sealing protrusions. The protrusions may extend radially outward. The method may include positioning the heart valve assembly at the implantation site with the sealing member aligned with an annulus. The heart valve assembly is deployed at the implantation site and the sealing member provides a sealing interface between the heart valve assembly and the annulus. The protrusions may provide a sealing or cupping function between the heart valve assembly and the annulus that limits black flow of blood. A method of providing a sealed interface between a heart valve assembly and an annulus at an implantation site may include similar method steps.

Another aspect of the present disclosure relates to a heart valve assembly that includes a heart valve, a self-expandable and collapsible stent, and a sealing member. The stent includes an inflow end and an outflow end and is configured to support the heart valve internally. The sealing member is connected to and extends circumferentially around the stent. The sealing member includes a plurality of radially outward extending protrusions comprising a fold of material of the sealing member.

The plurality of radially outward extending protrusions may be equally spaced apart around a circumference of the sealing member. The plurality of radially outward extending protrusions may include first and second axially spaced apart rows of the radially outward extending protrusions. The plurality of radially outward extending protrusions may be positioned at an inflow end of the stent. The plurality of radially outward extending protrusions may be arranged in at least one row extending around a circumference of the stent, wherein the at least one row is arranged at an angle relative to a longitudinal axis of the stent.

At least a portion of the sealing member may be positioned on the stent at a location distal of the heart valve. The sealing member may include a stitch pattern to form the plurality of radially outward extending protrusions. Each of the plurality of radially outward extending protrusions may include a plurality of stitches. The sealing member may include fabric. The sealing member may be mounted to a radially inward facing surface of the stent, and the plurality of radially outward extending protrusions may extend through the stent. The sealing member may be mounted to a radially outward facing surface of the stent. The stent may include annular, sinus and aortic sections, and the sealing member may be positioned at least partially along at least one of the annular and sinus sections. The sealing member may be connected to the heart valve. A central axis of the sealing member may be arranged at an angle relative to a longitudinal axis of the stent.

Another aspect of the present disclosure relates to a sealing member for use with a valve assembly. The sealing member includes a base configured for attachment to a self-expandable and collapsible stent. The plurality of protrusions are formed in a radially outward facing surface of the base and configured to provide a sealed interface between the valve assembly and an annulus at an implantation site.

The plurality of protrusions may include a fold in the base. The plurality of protrusions may include stitching. The sealing member may further include stitching secured to the sealing member to maintain a folded shape of the plurality of protrusions. The plurality of protrusions may be arranged in at least one row extending around the base.

Another aspect of the present disclosure relates to a method of manufacturing a valve assembly. The method includes providing a stent, a valve, and a sealing member. The stent has a self-expandable and collapsible construction. The sealing member includes a plurality of protrusions. The method further includes mounting the valve within the stent, and mounting the sealing member to the stent with the plurality of protrusions extending radially outward.

The method may also include forming the plurality of protrusions with a pattern of stitches secured to the sealing member. Mounting the sealing member to the stent may include positioning the sealing member within the stent. The method may also include arranging the plurality of protrusions in at least one row extending around a circumference of the sealing member.

As used in this specification and the appended claims, the term "engage" and "engagable" are also used broadly to mean interlock, mesh, or contact between two devices. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A heart valve assembly, comprising:
   a heart valve;
   a self-expandable and collapsible stent comprising an inflow end and an outflow end and being configured to support the heart valve internally, the stent having an inner surface, and an outer surface for contacting native heart tissue; and
   a sealing member disposed adjacent the inflow end of the stent and on the outer surface of the stent such that the sealing member extends circumferentially and entirely around the outer surface of the stent, the sealing member being attached to the stent at a plurality of attachment locations spaced about the stent in a circumferential direction to form a plurality of discrete protrusions comprising a fold of material of the sealing member, each of the plurality of discrete protrusions positioned between adjacent attachment locations in the circumferential direction and including a center portion that is positioned radially outward from the adjacent attachment locations, each of the center portions being compressible in a radially inward direction of the stent.

2. The heart valve assembly of claim 1, wherein the plurality of discrete protrusions are equally spaced apart in the circumferential direction of the stent.

3. The heart valve assembly of claim 1, wherein the plurality of discrete protrusions are circumferentially spaced about the stent in first and second rows, the first row being axially spaced apart from the second rows.

4. The heart valve assembly of claim 1, wherein the sealing member extends between a first edge adjacent the inflow end and a second edge closer to the outflow end than the first edge, the plurality of discrete protrusions positioned at the inflow end of the stent.

5. The heart valve assembly of claim 1, wherein the plurality of discrete protrusions are arranged in at least one row extending around the stent in the circumferential direction.

6. The heart valve assembly of claim 1, wherein at least a portion of the sealing member is positioned on the stent at a location distal of the heart valve.

7. The heart valve assembly of claim 1, wherein each of the discrete protrusions are disposed between two first stitchings located at the attachment locations and coupling the sealing member to the stent, and wherein each of the discrete protrusions include a second stitching coupled only to the discrete protrusion.

8. The heart valve assembly of claim 1, wherein each of the plurality of discrete protrusions includes a plurality of stitches.

9. The heart valve assembly of claim 1, wherein the sealing member comprises fabric.

10. The heart valve assembly of claim 1, wherein each of the discrete protrusions coincides with a shape of a cell of the stent.

11. The heart valve assembly of claim 1, wherein the sealing member is mounted to the outer surface of the stent.

12. The heart valve assembly of claim 1, wherein the stent includes annular, sinus and aortic sections, and the sealing member is positioned at least partially along at least one of the annular or the sinus sections.

13. The heart valve assembly of claim 1, wherein the sealing member is connected to the heart valve.

14. The heart valve assembly of claim 1, wherein a central axis of the sealing member is arranged at an angle of between 10 degrees and 30 degrees relative to a longitudinal axis of the stent so that the sealing member and the stent are not coaxial.

15. A sealing member for use with a valve assembly, comprising:
- a base configured and arranged to be entirely disposed radially outward of an outer surface of a self-expandable and collapsible stent, and capable of being attached about the outer surface of the stent such that the base is positioned between the outer surface of the stent and native heart tissue when the valve assembly is implanted at an implantation site; and
- a plurality of discrete protrusions disposed about the base in a circumferential direction and formed at least in part by at least one stitch, each of the plurality of discrete protrusions having a center portion positioned between two attachment regions and spaced radially outward from the two attachment regions, each center portions being compressible in a radially inward direction to provide a sealed interface between the valve assembly and a native annulus at the implantation site.

16. The sealing member of claim 15, wherein each of the plurality of discrete protrusions includes a fold in the base.

17. The sealing member of claim 15, wherein the at least one stitch maintains a folded shape of the plurality of discrete protrusions.

18. The sealing member of claim 15, wherein the plurality of discrete protrusions are arranged in at least one row extending around the base in the circumferential direction.

* * * * *